United States Patent
Bouguerfa

[19]

[11] Patent Number: 6,073,296
[45] Date of Patent: Jun. 13, 2000

[54] OPTICAL PROTECTIVE SCREEN WITH IMPROVED VISIBILITY

[76] Inventor: Maxime Bouguerfa, 8, rue du 14 juillet, 54260 Baslieux, France

[21] Appl. No.: 09/147,820
[22] PCT Filed: Sep. 11, 1997
[86] PCT No.: PCT/FR97/01604
 § 371 Date: Mar. 12, 1999
 § 102(e) Date: Mar. 12, 1999
[87] PCT Pub. No.: WO98/10877
 PCT Pub. Date: Mar. 19, 1998

[30] Foreign Application Priority Data

Sep. 13, 1996 [FR] France ................................. 96 11351
May 28, 1997 [FR] France ................................. 97 06721

[51] Int. Cl.[7] ................................. A61F 9/02; A42B 3/04
[52] U.S. Cl. ............................... 15/102; 15/256.5; 2/424; 2/438
[58] Field of Search .................... 15/100, 102, 256.5; 2/422, 438, 434, 424

[56] References Cited

U.S. PATENT DOCUMENTS

| | | | |
|---|---|---|---|
| 614,673 | 11/1898 | Taylor | 2/438 |
| 2,886,819 | 5/1959 | Uphoff | 2/438 |
| 4,021,878 | 5/1977 | Peillex | 2/438 |
| 4,179,756 | 12/1979 | Lucas | 2/434 |
| 4,428,081 | 1/1984 | Smith | 2/422 |
| 4,542,538 | 9/1985 | Moretti | 2/422 |
| 5,203,035 | 4/1993 | Lawlor | 2/434 |

FOREIGN PATENT DOCUMENTS

| | | | |
|---|---|---|---|
| 2427906 | 1/1975 | Germany | 2/438 |
| 2511243 | 9/1976 | Germany | 2/438 |

*Primary Examiner*—Randall E. Chin
*Attorney, Agent, or Firm*—Nixon Peabody LLP; Thomas W. Cole

[57] ABSTRACT

An optical protective screen for improved visibility is provided including an electric motor for moving a transparent sheet or film in a transport direction, which sheet or film is disposed in a field of vision of an optical apparatus or human observer. A cleaning mechanism formed from brushes or squeegees or the like, which are oriented generally transversely to the transport direction of the sheet or film are, disposed on at least one side of the field of vision and are applied against said sheet or film to clean it.

11 Claims, 5 Drawing Sheets

OPTICAL PROTECTIVE SCREEN WITH IMPROVED VISIBILITY

BACKGROUND OF THE INVENTION

The invention relates to an optical protective screen for improved visibility intended to be disposed in the field of view of an optical apparatus or a human observer.

Fine particles in motion, e.g. streams of dust or dirt, can deposit on a protective mask, window, lens, or the like, leading to reduced visibility which is a safety hazard e.g. for a motorcyclist.

A known protective device comprises a plurality of superposed thin transparent films, disposed on, e.g., the visor or mask of a motorcycle helmet. As each successive film becomes soiled, the motorcyclist removes it, exposing the next film. The overall thickness of the initial aggregate is limited, so as to avoid distortion of the field of view. Consequently, the useful life of one aggregate is limited, because the number of films which can be used in one aggregate is limited. Moreover, the motorcyclist must divert his attention while manipulating the device to remove a soiled film; this itself risks accidents.

Another known device which is applied to the visor or mask of a motorcycle helmet comprises a reel or the like, of transparent film, which is unrolled in front of the visor. Once the film is entirely used, it is replaced by reloading the device in a manner similar to reloading film in a photographic camera. The manipulations needed to replace the film in this device are somewhat complex. Also, the user is obliged to carry a spare reel of film, which is inconvenient.

SUMMARY OF THE INVENTION

The object of the present invention is to devise an optical protective screen which enables one to improve the visibility of a particular field of view, and which avoids the complex manipulations involved in film replacement, in that the inventive screen utilizes a cleaning system for the film.

The inventive screen which achieves this object is an optical protective screen for improved visibility, comprised of drive means to transport, move or displace, a transparent sheet or film in a transport direction, which sheet or film is disposed in a field of vision of an optical apparatus or a human observer; characterized in that cleaning means comprising brushes (or squeegees or the like hereinafter, "brushes"), oriented generally transversely to the transport direction of the sheet or film, are disposed on at least one side of the field of vision and are applied against said sheet or film.

As the film is being transported, the brushes rub against the film to remove soils and leave the film clean and clear. In this way, by cleaning and reusing the film, one avoids continual replacement of used film. Thereby one greatly increases the service life of the film. The inventive device is particularly well suited for providing improved visibility under difficult ambient conditions.

According to a particular embodiment, the screen is comprised of a frame (or housing) having a window opening, which frame has two enclosures disposed near the lateral sides of the window, wherewith the sheet or film comprises a film which is transported in the window between the two enclosures, the transporting being alternately in one direction and then the other, with the aid of drive means suitable for moving the film, and wherewith the brushes are disposed at or near the respective sides of the window.

With this embodiment, the cleaning is accomplished by contact of the brushes with the film, as the back-and-forth displacement of the film is carried out. The cleaning is improved by employing a plurality of brushes disposed against both faces of the film.

According to a first variant embodiment, the screen is comprised of two respective hollow reels disposed in the enclosures, wherewith the film is wound up onto and unwound from said reels.

The use of hollow reels provides spaces to accommodate the drive means, thereby reducing the overall dimensions and weight of the device, and reducing the number of parts needed for the drive means.

According to a second variant embodiment, the frame is comprised of storage components disposed at the aforesaid enclosures.

With this variant embodiment, part of the storage space is used to accommodate the film. As the film is transported, it is moved translationally in the interior of said space, instead of being wound up onto a reel. As an example, the storage components may comprise arms whereby the screen is mounted on a motorcycle helmet.

According to a preferred embodiment, the drive means comprise an electric motor disposed coaxially in one of said reels, designated the first reel, which first reel is connected via the film to a second reel having a (re)winding spring which spring is disposed on a support which is disposed coaxially on (or in) said second reel.

The use of electric motor drive means for transporting the film allows one to avoid manual manipulation. Manual manipulation is undesirable because it inevitably distracts the user's attention. The electric motor serves to drive the first reel, with one end of the film being wound onto said reel; at the same time, the other end of the film is unwound from the second reel. A spring, preferably a torsion spring, is disposed coaxially with and interiorly of the second reel, wherewith said spring is tensioned as the film is unwound from said reel.

Subsequently, the film is unwound from the first reel by reversing the rotational direction of the motor. During this process, the spring tension is utilized to automatically wind the film onto the second reel. As seen, the described drive system is a convenient means of generating alternate back-and-forth movement of the film. The spring also serves to maintain a slight tension in the film as film transport is carried out.

According to a fourth embodiment, the enclosures contain a cleaning liquid and are provided with sealing means to prevent leakage of said liquid, said sealing means comprising the brushes (or squeegees or the like) which are disposed at the respective sides of the film.

The combined use of a cleaning liquid and brushes results in a higher degree of cleaning and clarity of the film. The cleaning liquid may comprise a liquid which facilitates dissolution of the soils deposited on the film. Once the liquid has achieved its effect, the brushes then wipe away excess liquid present on the film. Leakage of the cleaning liquid from the enclosures is avoided by the sealing effect of the brushes.

According to a particular embodiment, the brushes are inclined with respect to the transport direction of the film.

With this embodiment, the inclination of the brushes tends to impel the soils to be removed in a preferred direction. As the film is displaced, the soils present on the film tend to force ahead the soils already accumulated on the brushes. Thus the inclined brushes more efficiently remove accumulated soils.

According to a preferred embodiment, the brushes are retracted out of contact with the film when the film is displaced in one direction, and are returned to their contacting status when the film is displaced in the other direction, so as to wipe away excess cleaning liquid; further, the screen has sealing means comprised of wiping-nubs (squeegees or the like), disposed transversely to the transport direction of the film, which nubs or the like serve to lightly pinch said film.

This embodiment serves to avoid a situation wherein, during the transporting of the film, soils present on the film accumulate in the vicinity of the brushes on the sides of the window, which accumulation can occur if the brushes are permanently held in contact with the film. As film transport proceeds, there is a risk that some of such accumulated soil material will be released by the brushes and picked up by the film, forming tracks or the like which are detrimental to good visibility. With the described embodiment, the brushes disposed on the lateral side where the film is being wound up onto a reel are retracted, such that when the film is being wound up the brushes do not wipe away soils, but subsquently when the film is being unwound from the reel the brushes are brought back into contact with the film, whereby soils are retained on the side of the brushes facing said reel, and excess cleaning liquid is removed. With this arrangement, the chance that soils will be returned to the field of vision is reduced. Moreover, soils have less tendency to accumulate (by agglomeration or the like) at the brushes, because the liquid promotes cleaning of the film (e.g. washing-away of soils from the film) before the brushes exert their wiping action.

Other advantages and features of the invention will be apparent from the following description of an inventive protective screen for improved visibility, with reference to the accompanying drawings. The described screen is particularly intended to be disposed on the visor or mask of a motorcycle helmet.

DETAILED DESCRIPTION OF THE PREFERRED EMBODIMENT

Figure 1:
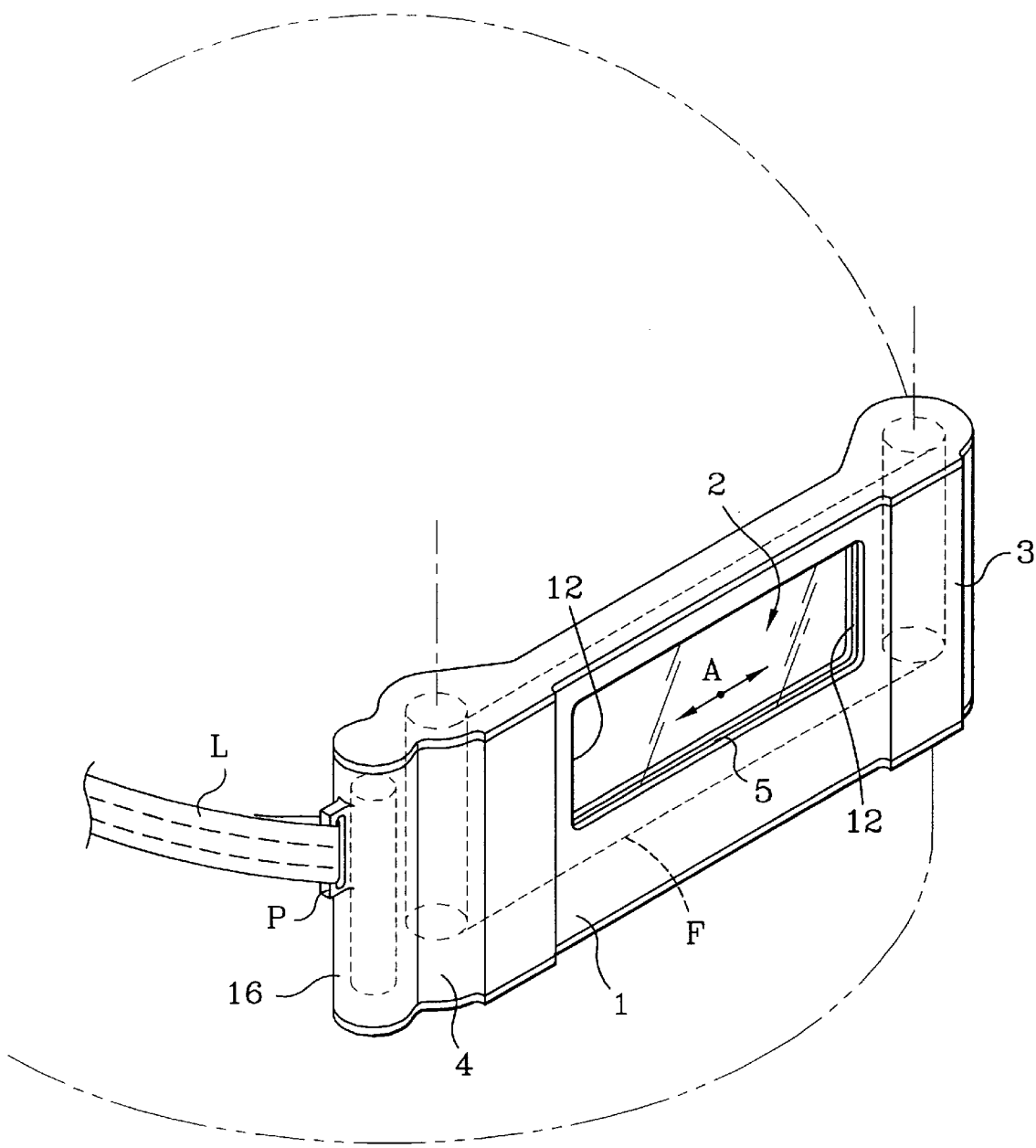
FIG. 1 is an overall perspective view of a protective screen disposed on a motorcycle helmet.

The protective screen illustrated in FIG. 1 is comprised of a frame 1 with a window opening 2 of (e.g.) rectangular shape, which opening is disposed in the field of view an individual, in particular on the visor or mask of the helmet of a motorcyclist. The screen is held in position on the visor or mask by means of an elastic strap L fixed to the frame 1 by attaching-lugs P.

Cavities in the housing 1 form a first enclosure 3 and a second enclosure 4 disposed beyond the respective lateral sides (12, 12) of the window 2. A transparent film F is advanced alternately toward one enclosure and toward the other, in the transport direction represented by arrow A. A slot 5 in frame 1 serves to guide the film in the window 2.

The screen is shown in FIG. 1 in operating position, with the direction of film transport being horizontal. Alternatively, if necessary, the screen can operate oriented vertically, with the enclosures being disposed horizontally and the transport direction of the film being vertical.

Figure 2:
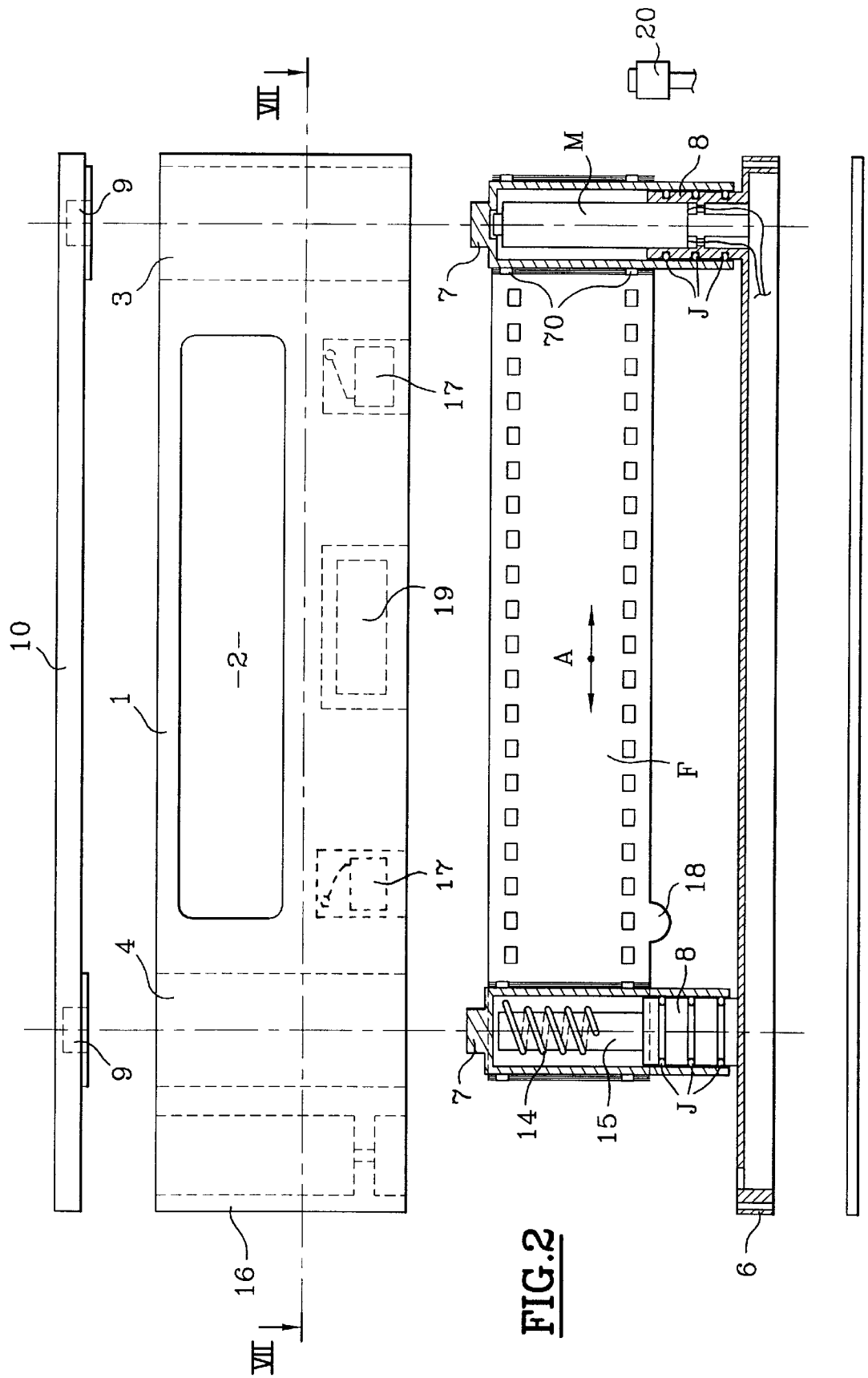
FIG. 2 is an exploded front view of the screen, showing in particular the driving means for the film, and the means of storing the film in reels.

As illustrated in FIG. 2, the frame has a bottom section 6 which bears hollow reels 7. In operation, the film F is alternately unrolled from and rolled onto these reels, which extend perpendicularly to the direction of transport of the film. The reels are housed in the aforementioned enclosures (3, 4).

The material of the film for the configuration shown is chosen to be somewhat flexible, e.g. comprising a polycarbonate, to ensure proper winding of the film on the reels.

The reels are guided in rotation by means of journals (8, 8) fixed to the bottom section 6. Each of these journals is inserted into the hollow in one end of the respective reel 7. The other end of each reel 7 is accommodated in a recess 9 in a cover 10.

The film F is transported by drive means comprising an electric motor M disposed coaxially in one of the reels 7 (a "first" such reel), which reel is connected via the film to the second reel, which second reel has a (re)winding spring 14 disposed on a support 15 disposed coaxially on said second reel. One of the ends of spring 14 is fixed to said second reel, and the other end is fixed to the support 15.

The drive transmission for the film is provided, in known fashion, by teeth 70 fixed to the reels 7, which teeth engage two parallel rows of openings in the lateral edge regions of the film, similar to the perforations in a photographic film.

The film is cleaned by means of cleaning elements illustrated schematically in FIG. 3, which elements comprise brushes (or squeegees or wipers —hereinafter, "brushes") 11 of the type used for cleaning glass. The brushes come into contact with the film F.

Figure 3:
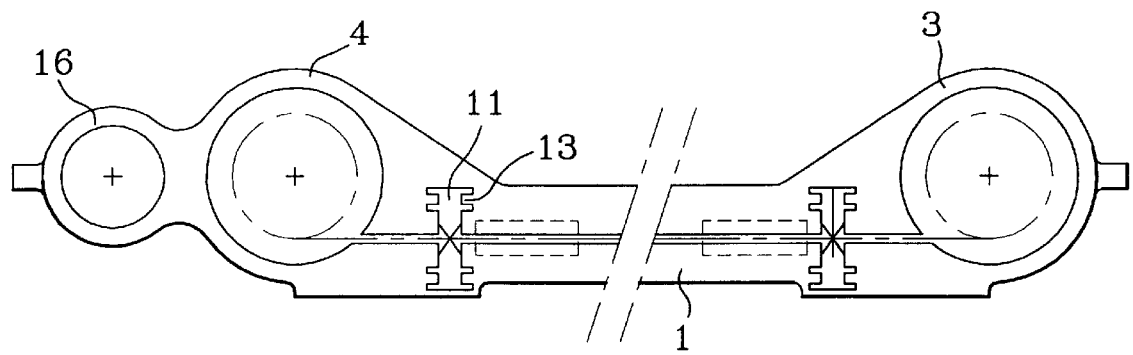
FIG. 3 is an overhead (plan) view of the screen with a cover thereof having been removed, showing in particular the mounting of the brushes which clean the film.

The brushes 11 are disposed transversely to the direction of transport of the film, against the two faces of the film, close to the lateral sides (12, 12) of the window 2. Said brushes 11 are fixedly anchored in grooves 13, wherewith the brushes can be easily replaced when worn. This replaceability allows substitution of other types of cleaning implements, such as rotating brushes, multiridge squeegees, felts, or sponges, whereby the cleaning means can be adapted to the conditions of use of the screen. It is also possible to employ a cleaning liquid, contained in the enclosures (3, 4), to improve the cleaning effectiveness in combination with the action of the brushes 11.

Where a liquid is used, in order to avoid leakage of the liquid, the enclosures (3, 4) are sealed with the aid of the brushes (squeegees or the like) 11 which are in contact with the film (FIG. 3). In addition, O-ring joints J (FIG. 2) are disposed between the journals 8 and the reels 7, to protect the electric motor M from penetration by the cleaning liquid.

The combination of the slots 5 which guide the film F and the brushes 11 which contact the film (FIG. 3) ensures that the film will be held in place under slight tension at times when the film drive is not active. This tension prevents unwinding of the film from the reels when, e.g., the wind blows against the window 2 while the user of the screen (along with the screen itself) is moving at high speed. Further, when the electric motor M is in a stopped status it prevents rotation of the first reel 7, whereby one end of the film can be immobilized. The other end of the film is subjected to the winding torque exerted by the spring 14 on the second reel, which torque applies tension to the film.

The electric motor is powered by a battery (not shown) disposed in a compartment 16 in the frame 1 which compartment can be opened to the outside, e.g. in order to replace the battery.

A switch 20, accessible from the exterior of the frame 1, is provided for stopping the transport of the film by interrupting the electric power supply to the battery.

The principle of operation of the protective screen will now be described, particularly the means of cleaning the film F according to the invention.

As mentioned, adverse weather conditions can result in various soils depositing on the film F, thereby reducing visibility. The user can initiate cleaning of the film by actuating the switch 20, causing the battery to supply power to the electric motor M.

As shown in FIG. 2, the electric motor which drives the film transport is controlled by a control circuit comprised of:

lever-type switches 17 configured so as to cooperate with a tab 18 on the film F, and a relay 19.

This control circuit is disposed interiorly of the frame 1. It enables back-and-forth transport of the film F, without interruption. The tab 18, as shown, is in contact with one of the switches 17 (designated the first lever switch 17).

The electric motor M then drives the first reel 7, whereby the film F is wound around said first reel. The second reel 7 is rotated via the intermediary of the film connected to the first reel, whereby the film F on said second reel is unwound from said second reel, with concomitant tensioning of the spring 14.

During i.e. near the end of this transport, the tab 18 actuates the second lever switch 17 by an action in the nature of a cam. Said second lever switch 17, causes the relay 19 to reverse the polarity of the electric power supply to the motor, causing the motor to reverse its direction of rotation. The film is now caused to unwind from the first reel, driven by both the motor M and the spring 14, wherewith said spring tends to cause the second reel to rotate whereby the film is wound onto said second reel. Eventually, during this (leftward movement in FIG. 2), the tab 18 re-engages the first switch 17, which switch causes the relay 19 to again reverse the polarity of the power supply to the motor M. Thereby the cycle of the film transport begins anew.

At any time, the user can interrupt the transport of the film by merely actuating the switch 20.

The control circuit may also be provided with means of varying the speed of film transport, in the course of a continuous or intermittent transport, depending on the conditions of use of the screen.

Figure 4:
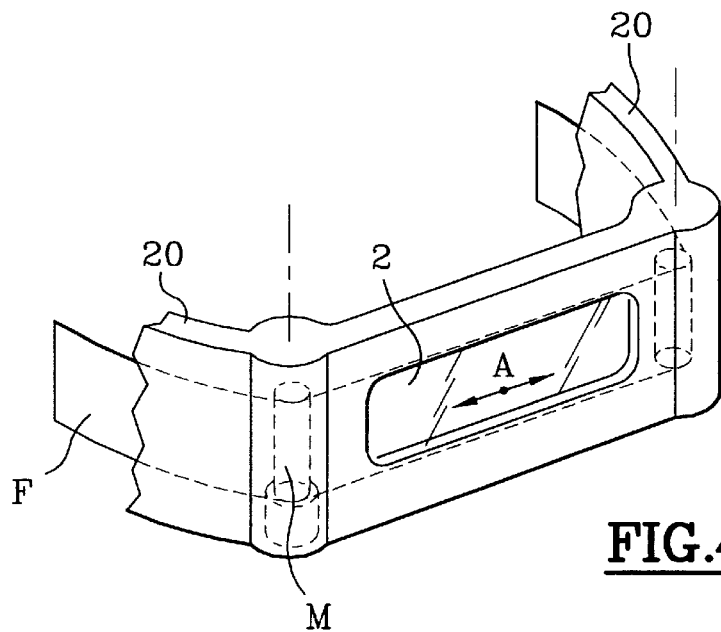
FIG. 4 is a perspective view showing a variant embodiment of the means of storage of the film.

FIG. 4 illustrates a variant embodiment in which the film F, as it is transported, is moved translationally in the interior of a storage component 20—not same as main switch 20, which component may comprise the arms which serve to hold the screen on the user's helmet. The back-and-forth transport of the film in the direction of the double arrow A is brought about by reversing the rotational direction of at least one motor M whereby the film is driven. The film is cleaned by the combination of the action of the brushes 11 and the transport of the film, as described supra.

Figure 5:
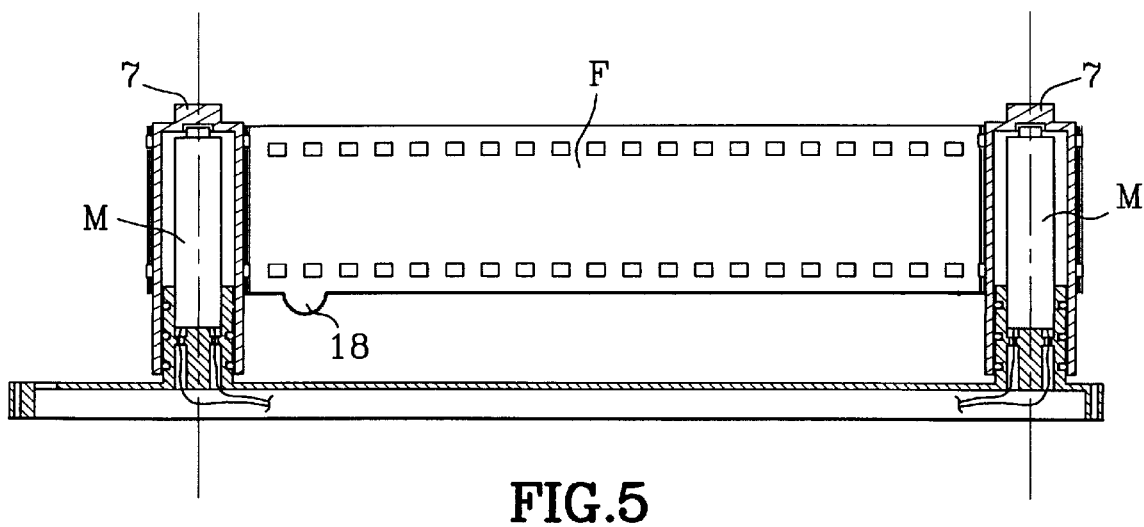
FIG. 5 is a view of the transport mechanism of the film corresponding to FIG. 2, in a variant wherein two electric motors are employed to drive the film.

FIG. 5 illustrates another variant, wherein two electric motors M are employed which are disposed in the interiors of the respective reels (7, 7) (designated the first reel and second reel). The control circuit is such as to enable simultaneous control of the two motors, whereby the film F can be wound around the first reel and unwound from the second reel; and wherewith the actuation of the lever-switch 17 causes a reversing of the motors, whereby the film F is now unwound from the first reel and wound around the second reel.

Means may also be provided whereby, during the winding or unwinding, the motors can be controlled so as to rotate at different speeds, wherewith the more slowly rotating reel provides resistance to the other reel, which other reel may be regarded as the driving wheel. In this way, tensioning of the film during the transport is assured.

In order to tension the film F when not being transported, the control circuit can cause the motors M to both tend to wind up the film, with the winding torques produced being of equal magnitudes but operating in opposite directions. These oppositely directed torques are applied to opposite ends of the film, to produce the desired tension.

Control means or the like may be provided to cause the two reels to rotate at different speeds in order to adjust to the variations in the effective radii of the two reels as the film is wound thereon (or unwound therefrom). Such variations of radii tend to result in variations in the tangential speeds of the reels 7 (even when only one motor M is employed), unless control means to adjust the angular speed(s) of rotation are implemented.

Figure 6:
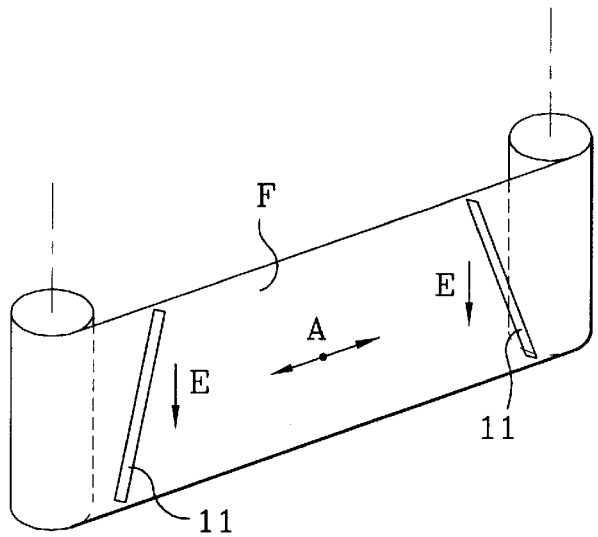
FIG. 6 is a schematic perspective view illustrating a variant in which the brushes are inclined so as to improve soils-removal.

As shown in FIG. 6, in order to be able to more effectively remove the soils (and/or excess cleaning liquid) at the level of the brushes, one can employ means of conferring a preferred direction of removal (arrow E); in particular, one can incline the brushes 11 with respect to the direction of transport of the film. In this way, as the film is displaced, the soils present on the film tend to force ahead the soils already accumulated on the brushes 11. These already accumulated soils, due to the combination of the influences of the inclination of the brushes and the direction of displacement, as well as gravity, tend to be removed downward. The described arrangement enables one to avoid excess accumulation of soils at the brushes 11, which would be detrimental to the cleaning action, resulting in a less-clean film.

Figure 7:
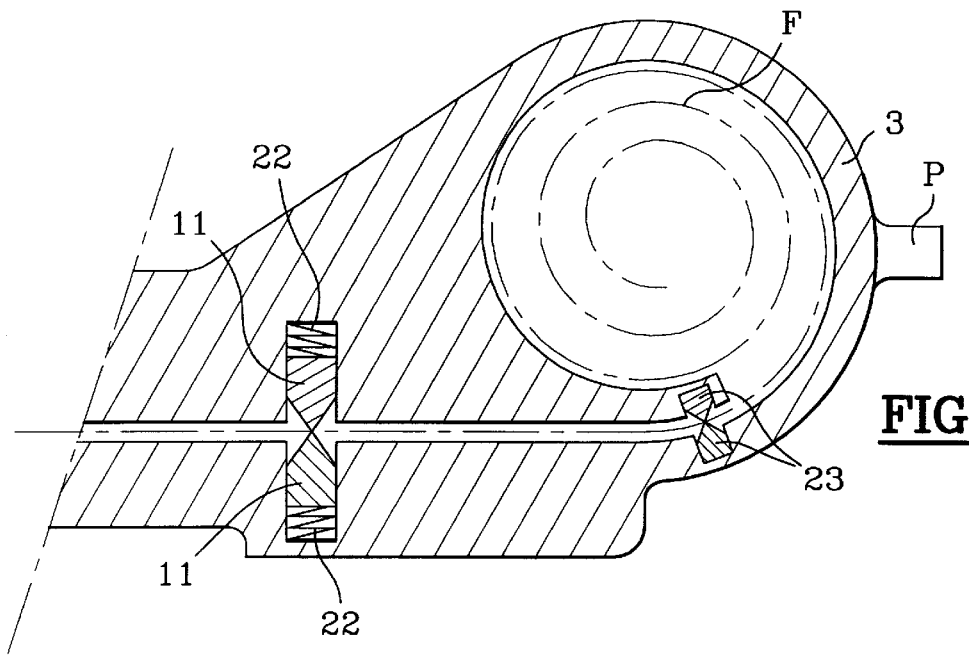
FIG. 7 is a partial cross sectional view through the line VII–VII of FIG. 2, showing a preferred variant embodiment employing retractably mounted brushes.

Another means of more effectively removing the soils (and/or excess cleaning liquid) is to arrange the brushes so as to be retractable, as illustrated in FIG. 7. One may provide cam means (not shown) fixed to the film, having a profile such as to cooperate with the brushes 11. As the film is transported, the cam means cause brushes disposed on the side where the film F is being wound up to be retracted, wherewith said brushes disengage so as to be completely out of contact with the film; when the film transport direction is changed such that the film is now being unwound on the side of the window where the brushes in question are disposed, the brushes are brought back into contact with the film, by the action of springs 22. The cleaning of the film is accomplished with the aid of cleaning liquid contained in the enclosures (3, 4), wherewith the brushes 11 serve principally to wipe away excess cleaning liquid from the film F.

To avoid leakage of cleaning liquid when the brushes 11 are in retraction, sealing of the enclosures is accomplished by means of wiping-nubs (squeegees or the like) 23 which are disposed transversely to the direction of transport of the film and which lightly pinch the film F, as shown in FIG. 7.

Figure 8:
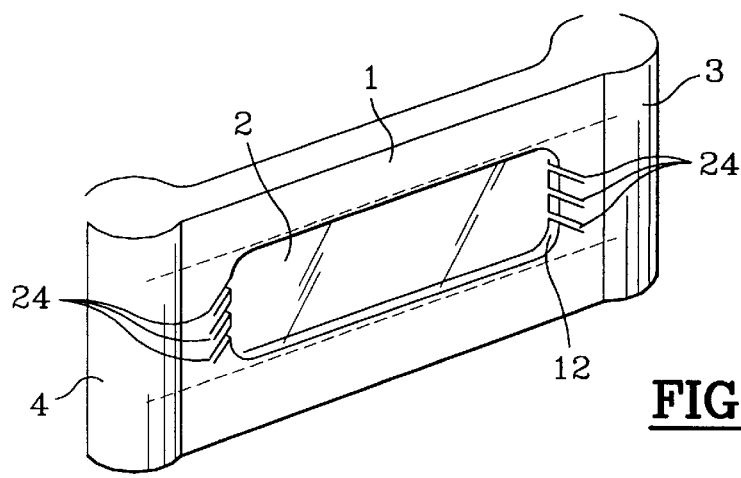
FIG. 8 is a schematic perspective view showing a variant employing channels for removal of soils and cleaning liquid.

FIG. 8 shows another (supplemental) means of avoiding major accumulation of soils at the brushes. Channels 24 are provided on the edges (12, 12) of the window 2. If one has an excess accumulation of soils which cannot be cleaned away by the brushes 11, these channels allow said excess to be carried away toward the exterior of the screen.

Figure 9:
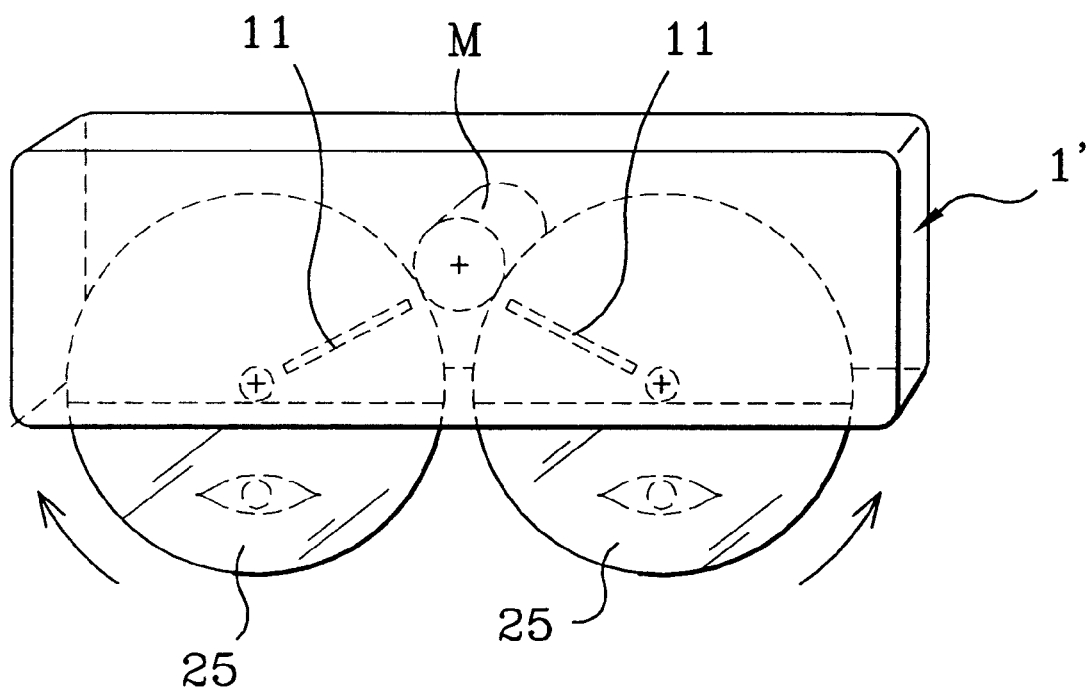
FIG. 9 is a schematic front view of an embodiment having a protective screen in the form of a pair of protective eyeglasses, utilizing sheets in the form of disks.

In the variant embodiment illustrated in FIG. 9, transparent sheets in the form of discs 25 are employed. The screen is essentially in the form of a pair of eyeglasses, having a frame 1' (which may be a parallelepiped-shaped box) which bears two discs 25. The discs 25 are axially parallel, with half of their extent disposed outside the frame 1' (e.g. as shown such that said lower half is disposed in front of the user's eyes), and the other half disposed inside the frame 1'. An electric motor M is disposed at a location generally between said two discs 25 and is oriented parallelly to the axes of the discs. The motor continuously rotates the discs in the opposite direction from the rotational direction of the motor, via a toothed pinion (not shown) which engages peripheral teeth (not shown) on the discs 25. Brushes 11 are disposed oriented radially along the discs, to effect cleaning. The frame 1' may contain a cleaning liquid to complement the action of the brushes.

The material of which the discs are comprised is chosen so as to be very rigid (e.g. polyvinyl chloride, PVC), to avoid deformation. It is possible to drive the discs 25 in alternate i.e. alternately directed angular displacements, wherewith the part of the disc which has just been cleaned is returned to the field of vision. With this arrangement, one may employ only a sector of a disc rather than an entire disc, thereby reducing the volume and weight of the screen device.

The invention is not limited to the exemplary embodiments described hereinabove.

In particular:

The protective screen may be disposed over an existing protective element, such as a windshield, wherewith the screen adds the feature of soil removal;

The protective screen may be installed so as to be removable, with the aid of suitable reversible fixing means, such as suction cups or other suction members, whereby, e.g., the visor or mask of a helmet can be removable;

The screen may be adapted to conform to the field of vision, e.g. the screen may curved for application to the curved visor or mask of a helmet;

The screen in the form of a disc or portion of a disc (as in the embodiment according to FIG. 9) may have variant shapes and forms, e.g. may have an elliptical or other shape rather than a circular disc-shape;

The lever-type switch 17 for the control circuit may readily be replaced by a photocell, phototransistor, or other mechanical or optical or electronic means capable of detecting the passage of the tab 18;

The brushes 11 may be disposed somewhat distant from the enclosures (3, 4) rather than being disposed near the lateral sides 12 of the window 2;

The film F may have a plurality of zones with dimensions generally equal to those of the window 2, wherewith said zones may be subjected to various mechanical or chemical treatments to improve the qualities of the film (e.g. anti-scratching, antifogging, polarizing, tinting) and in general render it adaptable to a variety of ambient and weather conditions;

The control circuit may comprise a programmable integrated circuit which can control the transport of the film so as to locate the various zones (mentioned above) in the window 2 as the user desires;

The teeth 70 which engage perforations in the film F may readily be replaced by axial openings in the reels, wherewith the ends of the film may penetrate into said openings; or the borders of the film may bear adhesive strips which adhesively bond them to the reels;

Mechanical means of driving the transport of the film may be provided instead of electrical; e.g., one may provide a ratchet mechanism operated by pulling laterally on a string or the like;

The protective screen may be configured generally as illustrated in FIG. 9 but with only a single disc;

The protective screen, in the form of a film or disc, may be employed in applications wherein reduced visibility is a safety risk, e.g. on visors (or masks) of helmets, goggles or the like, cameras, photographic apparatus, masks (such as industrial safety masks), headlights, beacons, automobile windshields, and rear-view mirrors; or the screen may be installed in a transparent housing which protects a machine tool of the type which uses a spraying system to distribute the cutting oil.

The invention relates to an optical protective screen for improved visibility, comprised of drive means to transport (move or displace) a transparent sheet or film in a transport direction, which sheet or film is disposed in a field of vision of an optical apparatus or human observer.

Cleaning means comprising brushes (or squeegees or the like), oriented generally transversely to the transport direction of the sheet or film, are disposed on at least one side of the field of vision and are applied against said sheet or film.

What is claimed is:

1. An optical protective screen for improved visibility, comprised of:

a drive mechanism for transporting a transparent sheet in a transport direction, which sheet is disposed in a field of vision of an optical apparatus or a human observer;

cleaning brushes oriented generally transversely to the transport direction of the sheet; said brushes being disposed on at least one side of the field of vision and applied against said sheet, and a frame having a window opening with lateral sides, which frame has two enclosures disposed near the lateral sides of the window, wherein the sheet includes a film which is transported in the window between the two enclosures, the transporting being alternately in one direction and then the other with aid of said drive mechanism, and the brushes being disposed at or near the respective sides of the window.

2. A screen according to claim 1, further comprising two respective hollow reels disposed in the enclosures wherewith the film is wound up onto and unwound from said reels.

3. A screen according to claim 2, wherein the drive mechanism includes an electric motor disposed coaxially in one of said reels, designated the first reel, which first reel is connected via the film to the other reel which has a rewinding spring that is disposed on a support disposed coaxially on said other reel.

4. A screen according to claim 2, wherein the drive mechanism includes two electric motors, each of which is disposed coaxially in a respective one of said reels.

5. A screen according to claim 1, wherein the frame includes storage components disposed at said enclosures.

6. A screen according to claim 1, wherein the enclosures contain a cleaning liquid and are provided with a seal to prevent leakage of said liquid, said seal including the brushes which are disposed at the respective sides of the film.

7. A screen according to claim 6, wherein the brushes are retractable when the film is displaced in one direction, and are extendable to a contacting status when the film is displaced in an opposite direction so as to wipe away excess cleaning liquid; and wherein the seal includes wiping-nubs that are disposed transversely to the transport direction of the film that can lightly pinch said film.

8. A screen according to claim 1, wherein the brushes are inclined with respect to the transport direction of the film.

9. A screen according to claim 1, wherein the enclosures include means for removal of soils, which means are disposed at the lateral sides of the window.

10. An optical protective screen for improved visibility, comprised of:

a drive mechanism for transporting a transparent sheet in a transport direction, which sheet is disposed in a field of vision of an optical apparatus or a human observer;

cleaning brushes oriented generally transversely to the transport direction of the sheet, said brushes being disposed on at least one side of the field of vision and applied against said sheet, wherein the sheet is present in the form of a disc driven in rotation; and the brushes are disposed along a radius of said disc.

11. An optical protective screen for improved visibility, comprising:

a drive mechanism for transporting a transparent sheet in a transport direction, which sheet is disposed in a field of vision of an optical apparatus or a human observer;

cleaning brushes inclined with respect to the transport direction of the sheet, said brushes being disposed on at least one side of the field of vision and applied against said sheet.

* * * * *